United States Patent [19]

Smith

[11] 4,150,053
[45] Apr. 17, 1979

[54] 2-DECARBOXY-2-AMINOMETHYL-6-HYDROXY-PGE$_1$ COMPOUNDS

[75] Inventor: Herman W. Smith, Kalamazoo Township, Kalamazoo County, Mich.

[73] Assignee: The Upjohn Company, Kalamazoo, Mich.

[21] Appl. No.: 918,524

[22] Filed: Jun. 23, 1978

Related U.S. Application Data

[63] Continuation-in-part of Ser. No. 812,794, Jul. 5, 1977, Pat. No. 4,131,738.

[51] Int. Cl.$^2$ ............................................. C07C 177/00
[52] U.S. Cl. ................................................. 260/563 R
[58] Field of Search ...................................... 260/563 R

[56] References Cited

U.S. PATENT DOCUMENTS

| | | | |
|---|---|---|---|
| 3,950,363 | 4/1976 | Bundy | 260/347.3 |
| 4,013,695 | 3/1977 | Lin | 260/410.9 R |
| 4,060,534 | 11/1977 | Bundy | 260/408 |

*Primary Examiner*—Gerald A. Schwartz
*Attorney, Agent, or Firm*—Robert A. Armitage

[57] ABSTRACT

The present invention provides 2-decarboxy-2-aminomethyl-6-hydroxy-PGE$_1$ compounds which are useful pharmacological agents. These analogs are useful as prostacyclin-like drugs.

34 Claims, No Drawings

2-DECARBOXY-2-AMINOMETHYL-6-HYDROXY-PGE$_1$ COMPOUNDS

CROSS REFERENCE TO RELATED APPLICATION

This application is a continuation-in-part of Ser. No. 812,794, filed July 5, 1977, now issued as U.S. Pat. No. 4,131,738.

The present invention relates to 2-decarboxy-2-aminomethyl-6-hydroxy-PGE$_1$ compounds, the preparation and use of which are described in U.S. Ser. No. 812,794, filed July 5, 1977, now issued as U.S. Pat. No. 4,131,738 on Dec. 26, 1978.

The essential material constituting a disclosure of the instant invention is incorporated by reference here from U.S. Pat. No. 4,131,738.

I claim:

1. A prostacyclin analog of the formula

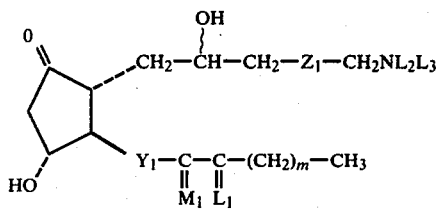

wherein L$_2$ and L$_3$ are hydrogen or alkyl of one to 4 carbon atoms, inclusive, being the same or different;
wherein Z$_1$ is
 (1) —(CH$_2$)$_g$—CH$_2$—CH$_2$—,
 (2) —(CH$_2$)$_g$—CH$_2$—CF$_2$—, or
 (3) trans-(CH$_2$)$_g$—CH=CH—,
 wherein g is the integer one, 2, or 3;
wherein Y$_1$ is
 (1) trans—CH=CH—,
 (2) cis—CH=CH—,
 (3) —CH$_2$CH$_2$—,
 (4) trans—CH=C(Hal)—, or
 (5) —C≡C—,
 wherein Hal is chloro or bromo;
wherein M$_1$ is

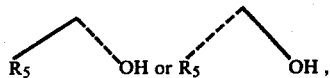

wherein R$_5$ is hydrogen or alkyl with one to 4 carbon atoms, inclusive;
wherein L$_1$ is

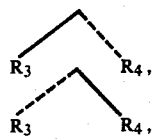

or a mixture of

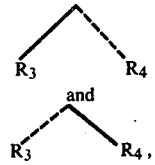

wherein R$_3$ and R$_4$ are hydrogen, methyl, or fluoro, being the same or different, with the proviso that one of R$_3$ and R$_4$ is fluoro only when the other is hydrogen or fluoro; and
wherein m is the integer one to 5, inclusive.

2. A prostacyclin analog according to claim 1, wherein ~ OH is beta.

3. 2-Decarboxy-2-aminomethyl-6β-hydroxy-PGE$_1$, a prostacyclin analog according to claim 2.

4. A prostacyclin analog according to claim 1, wherein ~ OH is alpha.

5. 2-Decarboxy-2-aminomethyl-6α-hydroxy-PGE$_1$, a prostacyclin analog according to claim 4.

6. 2-Decarboxy-2-aminomethyl-6α-hydroxy-15-methyl-PGE$_1$, a prostacyclin analog according to claim 4.

7. 2-Decarboxy-2-aminomethyl-6α-hydroxy-16,16-dimethyl-PGE$_1$, a prostacyclin analog according to claim 4.

8. 2-Decarboxy-2-aminomethyl-6α-hydroxy-16,16-difluoro-PGE$_1$, a prostacyclin analog according to claim 4.

9. A prostacyclin analog according to claim 1, wherein ~ OH is a mixture of α—OH and β—OH.

10. A prostacyclin analog according to claim 9, wherein Y$_1$ is cis—CH=CH—.

11. 2-Decarboxy-2-aminomethyl-6-hydroxy-cis-13-PGE$_1$, a prostacyclin analog according to claim 10.

12. A prostacyclin analog according to claim 9, wherein Y$_1$ is —C≡C—.

13. 2-Decarboxy-2-aminomethyl-6-hydroxy-13,14-didehydro-PGE$_1$, a prostacyclin analog according to claim 12.

14. A prostacyclin analog according to claim 9, wherein Y$_1$ is trans—CH=C(Hal)—.

15. 2-Decarboxy-2-aminomethyl-6-hydroxy-14-chloro-PGE$_1$, a prostacyclin analog according to claim 14.

16. A prostacyclin analog according to claim 9, wherein Y$_1$ is —CH$_2$CH$_2$—.

17. 2-Decarboxy-2-aminomethyl-6-hydroxy-13,14-dihydro-PGE$_1$, a prostacyclin analog according to claim 16.

18. A prostacyclin analog according to claim 9, wherein Y$_1$ is trans—CH=CH—.

19. A prostacyclin analog according to claim 18, wherein Z$_1$ is —(CH$_2$)$_g$—CH$_2$—CF$_2$—.

20. 2-Decarboxy-2-aminomethyl-2,2-difluoro-6-hydroxy-15-methyl-PGE$_1$, a prostacyclin analog according to claim 19.

21. A prostacyclin analog according to claim 18, wherein Z$_1$ is trans—(CH$_2$)$_g$—CH=CH—.

22. 2-Decarboxy-2-aminomethyl-trans-2,3-didehydro-6-hydroxy-PGE$_1$, a prostacyclin analog according to claim 21.

23. A prostacyclin analog according to claim 18, wherein Z$_1$ is —(CH$_2$)$_g$—CH$_2$—CH$_2$—.

24. A prostacyclin analog according to claim 23, wherein g is one.

25. A prostacyclin analog according to claim 24, wherein m is 3.

26. A prostacyclin analog according to claim 25, wherein R$_5$ is methyl.

27. 2-Decarboxy-2-aminomethyl-6-hydroxy-15-methyl-PGE$_1$, a prostacyclin analog according to claim 26.

28. A prostacyclin analog according to claim 25, wherein R$_5$ is hydrogen.

29. A prostacyclin analog according to claim 28, wherein at least one of R$_3$ and R$_4$ is fluoro.

30. 2-Decarboxy-2-aminomethyl-6-hydroxy-16,16-difluoro-PGE$_1$, a prostacyclin analog according to claim 29.

31. A prostacyclin analog according to claim 28, wherein at least one of R$_3$ and R$_4$ is methyl.

32. 2-Decarboxy-2-aminomethyl-6-hydroxy-16,16-dimethyl-PGE$_1$, a prostacyclin analog according to claim 31.

33. A prostacyclin analog according to claim 28, wherein R$_3$ and R$_4$ are both hydrogen.

34. 2-Decarboxy-2-aminomethyl-6-hydroxy-PGE$_1$, a prostaglandin analog according to claim 33.

* * * * *